United States Patent [19]

Ackermann et al.

[11] 4,013,656
[45] Mar. 22, 1977

[54] PROCESS FOR THE PREPARATION OF PYRIDYLAMINO-METHYLENEMALONIC ACID DERIVATIVES

[75] Inventors: Otto Ackermann, Troisdorf-Sieglar, Germany; Otto Bleh, deceased, late of Troisdorf-Bergheim, Germany, by Rita Bleh; Dieter Morgenstern, Troisdorf, Germany

[73] Assignee: Dynamit Nobel Aktiengesellschaft, Troisdorf, Germany

[22] Filed: Oct. 23, 1975

[21] Appl. No.: 625,287

Related U.S. Application Data

[63] Continuation of Ser. No. 365,815, May 31, 1973, abandoned.

[30] Foreign Application Priority Data

June 7, 1972 Germany .......................... 2227651

[52] U.S. Cl. .................. 260/294.9; 260/295 R; 260/295.5 R; 260/295.5 B
[51] Int. Cl.[2] .............. C07D 213/57; C07D 213/55
[58] Field of Search ................ 260/295.5 R, 295 R, 260/294.9, 295.5 B, 295 N

[56] References Cited

UNITED STATES PATENTS 3,585,198  6/1971  Meszaros et al. .................. 260/251

OTHER PUBLICATIONS

Lappin, J. Am. Chem. Soc., vol. 70, pp. 3348–3350, (1948).
The Merck Index, Eighth Edition, p. 711, RS 356 M524, 1968, C.8.

*Primary Examiner*—Alan L. Rotman
*Attorney, Agent, or Firm*—Burgess, Dinklage & Sprung

[57] ABSTRACT

A process for preparing a pyridylaminomethylenemalonic acid derivative of the formula:

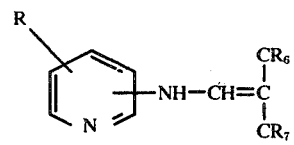

which comprises reacting together a pyridyl compound of the formula:

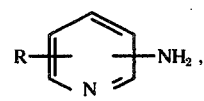

an alkoxy compound of the formula:

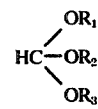

and a malonic acid derivative of the formula selected of the group of

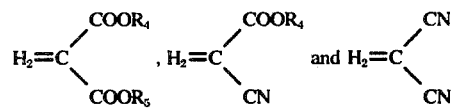

wherein:
$R_5$ and $R_7$ are the groups — $OOR_4$ or $OOR_5$ or = N
R is a substituted or unsubstituted alkyl radical, preferably a $C_1 - C_4$ alkyl radical;
$R_1$, $R_2$ and $R_3$ are each independently substituted or unsubstituted alkyl radicals, preferably $C_1 - C_2$ alkyl radicals;
$R_4$ and $R_5$ are each independently substituted or unsubstituted alkyl radicals, preferably $C_1 - C_8$ alkyl radicals at a temperature of 60° to 160° C.

15 Claims, No Drawings

PROCESS FOR THE PREPARATION OF PYRIDYLAMINO-METHYLENEMALONIC ACID DERIVATIVES

This is a continuation of application Ser. No. 365,815, filed May 31, 1973, now abandoned.

BACKGROUND OF THE INVENTION

1. Field of the Invention

This invention relates to the preparation of heterocyclic aminomethylene compounds by the reaction of aminopyridines with malonic acid derivatives and orthoformic acid trialkyl esters.

More particularly, this invention relates to the preparation of pyridylaminomethylenemalonic acid derivatives by a one-step process in which an aminopyridyl compound is reacted together with orthoformic acid trialkyl esters and a malonic ester. The present invention is particularly directed to the preparation of pyridylaminomethylenemalonic acids in high yields in excess of 90%.

2. Discussion of the Prior Art

It is known that, in the reaction of aminopyridines with alkoxymethylenemalonic acid esters that pyridylaminomethylenemalonic acid esters are formed together with alcohol. (cf. G. Lappin). Pursuant to such prior art processes, there is obtained yields which amount to about 90% as disclosed in Chemical Abstracts, Volume 66, page 268 (1967). The alkoxylmethylene malonic acid esters which are required for this reaction are prepared in a separate procedure or the condensation of orthoformic acid esters with compounds containing active methylene groups, in the presence of a catalyst. Condensation catalysts employed include acetic acid anhydride and, when malonic esters are used, anhydrous zinc chloride as well (cf. Berichte 26, 2729 (1893) and Annalen 279, 16 (1897). In this known process there is necessarily involved two reaction steps for the formation of the pyridylaminomethylenemalonic compounds. These reaction steps are as follows:

1. Initially the alkoxymethylene compound is prepared from orthoformic acid esters and malonic acid derivatives in the presence of a catalyst. The products that form are isolated generally by a fractional distillation process carried out in a fine vacuum column. The yields in this step of the desired alkoxymethylene compounds run between 65 and 85% of theory, based upon the malonic ester derivative.

2. After the alkoxymethylene compound is separated from the first step, it is condensed with aminopyridines.

As a result of this two-step process the yield per unit volume per unit of time is low and the yield of end product, referred to the malonic acid ester input, is only about 60 to 75% of theory.

Accordingly, it became desirable to provide a process wherein the yield of pyridylaminomethylenemalonic acid derivative, referred to the malonic acid ester input was substantially better than 75%. Moreover, it became desirable to provide a one-step process for the synthesis of such pyridylaminomethylenemalonic acid derivatives from aminopyridine compounds, orthoformic acid esters and esters of malonic acid. It became desirable to provide such a process which could be carried out in the absence of a catalyst.

SUMMARY OF THE INVENTION

The long-felt desires of the art have been satisfied by a process for preparing a pyridylaminomethylenemalonic acid derivative of the formula:

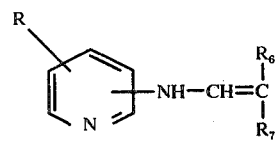

which comprises reacting together a pyridyl compound of the formula:

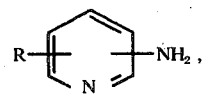

an alkoxy compound of the formula:

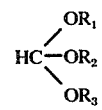

and a malonic acid derivative of the formulas selected of the group of

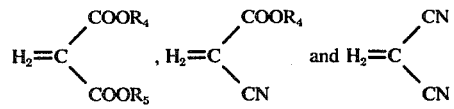

wherein:
R is a substituted or unsubstituted alkyl radical;
$R_1$, $R_2$ and $R_3$ are each independently alkyl radicals substituted or unsubstituted; and
$R_4$ and $R_5$ are each independently substituted or unsubstituted alkyl radicals
$R_6$ and $R_4$ are the groups $OOR_4$ or $OOR_5$ or $\equiv N$ at a temperature of 60 to 160° C.

A process has now been found for the preparation of pyridylaminomethylenemalonic acid derivatives which is characterized by the fact that aminopyridines are reacted together with malonic acid derivatives and orthoformic acid esters. Preferably, the orthoformic acid esters are present in the reaction mixture in a more than stoichiometric amount. Thus, the ratio of orthoformic acid ester to aminopyridine to malonic acid ester is generally in the range of 1 to 6: 1: 1 to 2. The above refers to a mole ratio of these reactants.

The process of the present invention is carried out at only mildly elevated temperatures such as between 60° and 160° C. Moreover, the use of a catalyst at any stage is unnecessary. The process is a one-step process carried out in a standard reaction vessel over a period of time of between 1 and 12 hours.

It has been surprisingly found that this reaction, in which no catalysts are employed, produces the desired pyridylaminomethylenemalonic acid derivatives in yields of about 96% with reference to the malonic acid derivatives. The reaction takes place in accordance with the following equation:

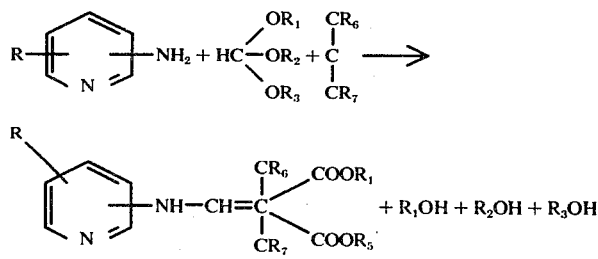

$$\text{R}-\underset{\text{N}}{\underset{|}{\bigcirc}}-\text{NH}-\text{CH}=\overset{\text{CR}_6}{\underset{\text{CR}_7}{\text{C}}}\overset{\text{COOR}_1}{\underset{\text{COOR}_5}{}} + \text{R}_1\text{OH} + \text{R}_2\text{OH} + \text{R}_3\text{OH}$$

In the above formula R is a substituted or unsubstituted alkyl radical generally a $C_1$–$C_8$ alkyl radical and preferably a $C_1$–$C_4$ alkyl radical. Normally, $R_1$, $R_2$ and $R_3$ are the same groups. However, they can be different. Thus, each can be a substituted or unsubstituted alkyl radical. Preferably, they are the same alkyl radical and the alkyl radical is a $C_1$–$C_2$ alkyl radical. Similarly, $R_4$ and $R_5$ as in the radicals $R_6$ and $R_7$ are normally the same alkyl radical. However, they can be different alkyl radicals. Each can independently be a substituted or unsubstituted alkyl radical. Preferably, the alkyl radical is an unsubstituted $C_1$–$C_8$ alkyl radical.

One of the more surprising developments which stemmed from the present invention, involves the finding that only a small amount of forminino compounds are synthesized as by-products in the reaction. This is surprising since those skilled in the art had expected that under the reaction conditions employed, 60° to 160° C, relatively large amounts of forminino compounds would have been synthesized due to the reaction of the aminopyridine with the orthoformic acid esters.

The present process has as its primary advantage the fact that it is a one-step process in which the three reactants can react together. Additionally, a further advantage resides in the ability to recover unreacted input components virtually quantitatively. This is difficult in the prior art processes, at least in the first step, owing to the presence of acetic acid anhydride. Advantageous use can be made of unreacted input components, pursuant to the present invention, by filtering out the desired reaction product, distilling all or part of the alcohol out of the mother liquor, and recycling the alcohol-free mother liquor to the next batch.

A further advantage of the present invention resides in the fact that the reaction can be carried out in the absence of an added solvent. The reaction mixture is already greatly diluted by the alcohol that forms during the process. Fortunately, the pyridylaminomethylenemalonic acid compounds prepared are insoluble in this alcohol and can be readily separated therefrom by known means, as by filtration.

DESCRIPTION OF SPECIFIC EMBODIMENTS

It has been stated above that the various alkyl residues or radicals of the reactants can be substituted as well as unsubstituted. When substituted, they can be substituted by any of the following moieties: methoxy; ethoxy.

Aminopyridines, malonic acid derivatives and orthoformic acid esters are used as starting products for the process of the invention. The orthoformic acid ester is to be present in a quantity that is greater than the stoichiometrically computed amount. The preferred molar ratio of aminopyridine to orthoformic acid ester ranges from 1:2 to 1:4. The ester compound of the orthoformic acid ester is preferably the methyl or ethyl ester.

The esters of malonic acid and cyanacetic acid ester are preferably used as the malonic acid derivatives. The methyl and ethyl esters are mentioned by way of example, but higher esters, such as the amyl, hexyl or octyl esters of malonic acid, can also be used. The molar ratio of aminopyridines to malonic acid derivatives is 1:1 to 2, preferably 1:1.05.

The amino group of the aminopyridines is located preferably in the 2 position; the reaction, however, can also be carried out with aminopyridines whose amino group is in a different position such as in the 3 or 4 position.

The aminopyridines can also be alkyl-substituted if desired, the alkyl group being able to have 1 to 4 carbon atoms.

In the process of the invention, the formation of undesired by-products is largely prevented by the excess of formic acid ortho ester and by precise control of the conditions of the reaction. The reaction is performed at temperatures not exceeding 160° C. At temperatures above 160° C, increasing amounts of undesired by-products form, which cannot be removed from the crude product by subsequent recrystallization, for example. At temperatures below 60° C the reaction takes too long, because the lower the temperature is, the slower is the reaction. The reaction can be carried out at atmospheric pressure or at elevated pressure. When elevated pressure is used, the pressure is between 1 atm and 20 atm.

The practical performance of the process is best carried out in a reaction kettle that is equipped with a mechanical stirring means, a means of measuring the temperature of the reaction solution, valves for feeding the reaction components, and a heating and cooling apparatus. This kettle is charged with the three reaction components in the stated molar ratio and carefully heated, with stirring, to 100° to 150° C. After about 2 to 4 hours, the reaction has ended.

Then the reaction solution is slowly cooled with stirring. The reaction product that crystallizes is separated by known methods, simply by centrifugation or filtration from the reaction solution. The filter cake is repeatedly washed with alcohol and the washing liquid is combined with the remaining mother liquor.

The alcohol is removed from the mother liquor by distillation and the remainder of the mother liquor left in the sump is recycled to the next batch.

The pyridylaminomethylenemalonic acid derivatives obtainable by the present process are valuable intermediates in the production of naphthyridine derivatives (e.g., nalidixinic acid and its derivatives). These end products find many applications based on their bacteriostatic properties. (see U.S. Pat. No. 3,149,104)

The so formed pyridylaminomethylenemalonic acid derivatives are converted to naladixinic acid by the following steps; described in J. Am. Chem. Soc., 70, 3348 (1948).

In order to more fully illustrate the nature of the invention in the manner of practising the same, the following Examples are presented.

EXAMPLE 1

Preparation of methylpyridylaminomethylenemalonic acid diethyl ester

The reaction vessel with a capacity of 6 liters was charged with 600 parts of 2-amino-6-methylpyridine, 930 parts of malonic acid diethyl ester and 2800 parts of orthoformic acid triethyl ester. Then the mixture was heated with stirring to about 130° C. After about 3 hours the reaction had ended.

The reaction solution was slowly cooled and the crystallized methylpyridylaminomethylenemalonic acid diethyl ester was centrifuged. The filter cake was repeatedly washed with alcohol and the washing liquids were combined with the filtrate. The ethanol was removed by distillation from this solution. The mother liquor left in the sump of the column was recycled with the next batch.

In this manner 100 batches were processed successively before it was necessary to free the mother liquor of by-products. In each new batch only the consumed portion of the starting product was replaced.

For the preparation of 130 kg of methylpyridylaminomethylmalonic acid diethyl ester with a melting point of 107° C, a total amount of 49.8 kg of 2-amino-6-methylpyridine, 78.0 kg. of malonic ester and 73.5 kg of orthoformic acid triethyl ester was consumed. This corresponded to an average yield, referred to methylaminopyridine, of 98%, of 96% with reference to malonic acid diethyl ester, and 94% of the theory with reference to orthoformic acid diethyl ester.

EXAMPLE 2

Preparation of methylpyridylaminomethylenecyanacetic acid ethyl ester 540 parts of 2-amino-6-methylpyridine, 625 parts of cyanacetic acid ethyl ester and 2,300 parts of orthoformic acid triethyl ester were heated to about 130° C in a reaction vessel equipped with a column and a stirrer. During the reaction the alcohol that formed was distilled out of the reaction solution through the head of the column within about 5 hours.

After the reaction had ended the mixture was cooled in an ice bath, the crystallized methylpyridylaminomethylenecyanacetic acid ethyl ester was filtered out and washed with alcohol. The filtrates were combined with the washing liquid and recycled with the next batch as described in Example 1. The average yield of five batches amounted to 1,131 parts of the above-named product per batch.

EXAMPLE 3

Preparation of pyridylaminomethylenemalonic acid diethyl ester

The reaction vessel was charged with 564 parts of 2-aminopyridine, 1,008 parts malonic acid diethyl ester and 3,110 parts orthoformic acid triethyl ester and heated with stirring at about 130° C. In the course of the reaction the ethanol that formed was distilled out of the reaction mixture through a short column within 4 to 5 hours. Then most of the unreacted orthoformic acid triethyl ester was evaporated from the solution, first at atmospheric pressure and then at 40 mm Hg. After the mixture was cooled, the crystallized pyridylaminomethylenemalonic acid diethyl ester was filtered out and repeatedly washed with alcohol. The filtrate and the washing liquids were combined and, after the distillation process described in Example 1, they were recycled with the next batch. The yield of the above-named product amounted to 96% of the theory with reference to amino-pyridine.

EXAMPLE 4

Preparation of methylpyridylaminomethylenemalonic acid dimethyl ester 648 parts of 2-amino-6-methylpyridine, 810 parts of malonic acid dimethyl ester and 2,500 parts or orthoformic acid trimethyl ester were heated for 6 hours with stirring, at 130° to 140° C. Then the reaction mixture was cooled in an ice bath and the crystallized ester was removed by filtration. The filter cake was recrystallized from methanol-trimethylorthoformiate and then washed with ethanol.

The combined solutions were treated as described in Example 1.

In the manner described, five batches were performed successively. The average yield per batch amounted to 1,360 parts of methylpyridylaminomethylenemalonic acid dimethyl ester; this corresponded to a yield of about 91% of the theory with reference to methylaminopyridine, and 89% of the theory with reference to malonic acid dimethyl ester.

We claim:

1. A process for preparing a pyridylaminomethylenemalonic acid derivative of the formula:

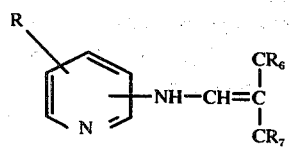

which comprises reacting together a pyridyl compound of the formula:

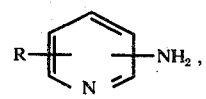

an alkoxy compound of the formula;

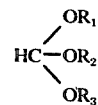

and a malonic acid derivative of the formulas selected of the groups of

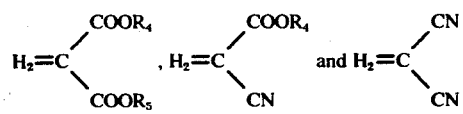

wherein:

$R_6$ and $R_7$ and the groups $OOR_4$ or $OOR_5$ or $=N$

R is hydrogen or unsubstituted $C_1$–$C_4$ alkyl radical;

$R_1$, $R_2$ and $R_3$ are each independently methoxy or ethoxy substituted or unsubstituted $C_1$–$C_2$ alkyl radicals;

$R_4$ and $R_5$ are each independently methoxy or ethoxy substituted or unsubstituted $C_1$–$C_8$ alkyl radicals at a temperature of 60 to 160° C.

2. A process according to claim 1 wherein the pyridyl compound, the alkoxy compound and the malonic acid ester compound are reacted in a one-step process and said pyridylaminomethylenemalonic derivative is recovered from the reaction mixture.

3. A process according to claim 1 wherein the reaction is carried out while alcohol so formed during the process is removed by distillation.

4. A process according to claim 1 wherein the alkoxy compound is present in a more than stoichiometric amount.

5. A process according to claim 1 wherein the molar ratio of pyridyl compound: malonic acid ester: alkoxy compound is 1:1 to 2:1 to 5.

6. A process according to claim 1 wherein the reaction is carried out under a pressure between 1 and 20 atm.

7. A process according to claim 1 wherein the malonic acid ester is malonic acid diethyl ester and the alkoxy compound is orthoformic acid triethyl ester and the pyridyl compound is 2-amino-6-methylpyridine.

8. A process according to claim 1 wherein the pyridyl compound is 2-amino-pyridine, the malonic acid ester is malonic acid diethyl ester and the alkoxy compound is orthoformic acid triethyl ester.

9. A process according to claim 1 wherein the pyridine compound is 2-amino-6-methylpyridine, malonic acid dimethyl ester is the malonic acid ester and the alkoxy compound is orthoformic acid trimethyl ester.

10. A process for preparing a pyridylaminomethylenemalonic acid derivative of the formula

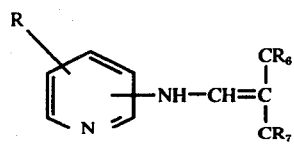

which comprises reacting together a pyridyl compound of the formula

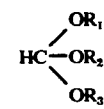

an alkoxy compound of the formula $$HC\begin{matrix}OR_1\\ OR_2\\ OR_3\end{matrix}$$

and a malonic acid derivative of the formula selected from the groups of

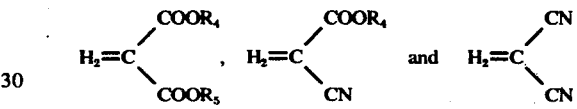

wherein:

$R_6$ and $R_7$ are the groups $OOR_4$ or $OOR_5$ or $=N$;

R is unsubstituted $C_1$–$C_4$ alkyl radical;

$R_1$, $R_2$ and $R_3$ are each independently methoxy or ethoxy substituted or unsubstituted $C_1$–$C_2$ alkyl radicals;

$R_4$ and $R_5$ are each independently methoxy or ethoxy substituted or unsubstituted $C_1$–$C_8$ alkyl radicals at a temperature of 60° to 160° C.

11. A process for preparing a pyridylaminomethylenemalonic acid derivative according to claim 1 wherein the R radical is at the 6th position.

12. A process according to claim 11 wherein R is methyl.

13. A process according to claim 1 wherein the amino group of the pyridyl compound is at the 2 position.

14. A process according to claim 1 wherein the amino group of the pyridyl compound is at the 3 or 4 position.

15. A process according to claim 1 wherein R is hydrogen.

* * * * *

UNITED STATES PATENT AND TRADEMARK OFFICE
CERTIFICATE OF CORRECTION

PATENT NO. : 4,013,656
DATED : March 22, 1977
INVENTOR(S) : Otto Ackermann et al It is certified that error appears in the above—identified patent and that said Letters Patent are hereby corrected as shown below:

Column 3, line 66, before "greater" insert -- generally --.

Signed and Sealed this

Fourteenth Day of June 1977

[SEAL]

Attest:

RUTH C. MASON
Attesting Officer

C. MARSHALL DANN
Commissioner of Patents and Trademarks